(12) United States Patent
Hashiba et al.

(10) Patent No.: US 7,854,167 B2
(45) Date of Patent: Dec. 21, 2010

(54) STATOR CORE LOOSENING DIAGNOSIS DEVICE AND STATOR CORE LOOSENING DIAGNOSIS METHOD

(75) Inventors: Yutaka Hashiba, Kanagawa (JP); Norio Takahashi, Kanagawa (JP); Masayuki Ichimonji, Tokyo (JP); Hitoshi Katayama, Kanagawa (JP); Takaharu Tani, Kanagawa (JP); Tatsuo Taniguchi, Tokyo (JP); Masayuki Takahashi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 415 days.

(21) Appl. No.: 12/122,348

(22) Filed: May 16, 2008

(65) Prior Publication Data
US 2008/0282803 A1   Nov. 20, 2008

Related U.S. Application Data

(63) Continuation-in-part of application No. PCT/JP2006/322728, filed on Nov. 15, 2006, now abandoned.

(30) Foreign Application Priority Data
Nov. 16, 2005   (JP) .............................. 2005-330993

(51) Int. Cl.
*G01M 7/02* (2006.01)
(52) U.S. Cl. .............................. 73/572; 73/579; 73/602
(58) Field of Classification Search .................. 73/572, 73/579, 602, 862.23, 862.41, 862.593
See application file for complete search history.

(56) References Cited

U.S. PATENT DOCUMENTS

| | | | | |
|---|---|---|---|---|
| 4,425,523 A | * | 1/1984 | Detinko et al. | 310/433 |
| 4,663,553 A | * | 5/1987 | Zimmermann | 310/419 |
| 4,709,182 A | * | 11/1987 | Wenske et al. | 310/316.01 |

(Continued)

FOREIGN PATENT DOCUMENTS

JP          57-168977          10/1982

(Continued)

OTHER PUBLICATIONS

Huang Ge, "Discussions on Damage Detection of a Spatial Composite-Structure Beam Using Vibration Modal Parameters", China Academic Journal Electronic Publishing House, May 2005, 11 pages (with English Translation).

*Primary Examiner*—Jacques M Saint Surin
(74) *Attorney, Agent, or Firm*—Oblon, Spivak, McClelland, Maier & Neustadt, L.L.P.

(57) ABSTRACT

A diagnosis device for diagnosing loosening of a stator core of a rotary electrical machine. The diagnosis device has: excitation means for vibrating the stator core in the radial direction; vibration detection means for detecting the vibration of the stator core in the radial direction; means for frequency-analyzing an output signal of the vibration detection means that detects vibration generated in the stator core when the stator core is vibrated by the excitation means so as to extract a measurement natural vibration mode of the stator core in a circular ring natural vibration mode; means for estimating a circular ring natural vibration mode of the stator core from shape data of the stator core; and means for determining a clamping state of the stator core by comparing the measurement natural vibration mode and a determination criterion obtained based on the estimated natural vibration mode.

23 Claims, 16 Drawing Sheets

U.S. PATENT DOCUMENTS

| | | | | |
|---|---|---|---|---|
| 4,887,474 A | * | 12/1989 | Sargeant | 73/865.9 |
| 4,901,572 A | * | 2/1990 | Suyama | 73/572 |
| 5,295,388 A | * | 3/1994 | Fischer et al. | 73/12.09 |
| 5,493,894 A | * | 2/1996 | Dailey et al. | 73/12.09 |
| 5,615,575 A | * | 4/1997 | Goodwin | 73/862.541 |
| 6,924,650 B2 | * | 8/2005 | Haeusermann et al. | 324/546 |
| 7,741,854 B2 | * | 6/2010 | Humphries et al. | 324/546 |
| 7,743,675 B2 | * | 6/2010 | Moore | 73/865.8 |

FOREIGN PATENT DOCUMENTS

| | | |
|---|---|---|
| JP | 59-061449 | 4/1984 |
| JP | 01-218338 | 8/1989 |
| JP | 10-082714 | 3/1998 |
| JP | 2000-354353 | 12/2000 |

* cited by examiner

STATOR CORE LOOSENING DIAGNOSIS DEVICE AND STATOR CORE LOOSENING DIAGNOSIS METHOD

CROSS REFERENCES TO RELATED APPLICATIONS

This is a continuation-in-part of Application PCT/JP2006/322728, filed on Nov. 15, 2006, now abandoned. This application is based upon and claims the benefit of priority from the prior Japanese Patent Application No. 2005-330993, filed in the Japanese Patent Office on Nov. 16, 2005, the entire content of which is incorporated herein by reference.

BACKGROUND OF THE INVENTION

The present invention relates to a diagnosis device for diagnosing loosening of a stator core of a rotary electrical machine and its diagnosis method.

In general, in a stator of a rotary electrical machine such as an electric generator or an electric motor, a stator core is configured by laminating thin electromagnetic steel sheets having, on its inner radial side, a space into which a coil is inserted and clamping the laminated electromagnetic steel sheets in the axial direction. Then, a coli is inserted into a coil insertion space on the inner radial side of the electromagnetic steel sheets and is connected outside the stator core.

In the stator core having such a configuration, insufficient clamping of the stator core may decrease a clamping specific pressure of the laminated electromagnetic steel sheets. Accordingly, the electromagnetic steel sheets vibrate, so that insulating layers coated on the surface of the electromagnetic steel sheets may be separated therefrom due to rubbing and beating between the electromagnetic steel sheets, causing an electrical connection to be established between the electromagnetic steel sheets. As a result, an eddy current is induced and, in the worst case, the stator core undergoes melting damage. In order to prevent this, it has been necessary not only to assembling the stator core while adequately controlling the stator core specific pressure in the manufacturing process, but also to periodically check/inspect the stator core specific pressure in a plant in operation. Conventionally, in this inspection, a jig having a thin knife-like shape is inserted in a gap between the electromagnetic steel sheets, and the clamping state of the stator core is sensuously judged by the insertion condition. However, the judgment depends on the feeling of individual inspectors, so that a lot of skill is required for the judgment. Further, the judgment varies between individuals, resulting in a variation of quality.

In order to cope with this problem, Japanese Patent Application Laid-Open Publication No. 2000-354353, the entire contend of which is incorporated herein by reference, discloses a method of quantitatively evaluating the clamping state of the stator core. This method inserts a torque wrench into the air duct portion which is generally provided for cooling of the stator core of a rotary electrical machine and measures a torque value indicated by the torque wrench and displacement amount of the stator core or torque wrench obtained at the time when the torque wrench is inserted into the stator core to thereby numerically evaluate the stator core specific pressure.

As described above, it is necessary to insert the torque wrench into the air duct portion in the method disclosed in Patent Document 1. However, the air duct of this type generally has a narrow width and therefore a torque wrench formed in an extremely thin shape is required. On the other hand, the clamping specific pressure of the stator core is extremely high, so that when such a torque wrench formed in an extremely thin shape is used, the toque wrench itself is deformed. As a result, a sufficient external force cannot be applied to the stator core, making it impossible to evaluate the stator core clamping pressure properly.

Further, the torque wrench can apply an external force only to a small portion of the stator core, so that the stator core clamping pressure that can be evaluated is limited to a small portion of the stator core, i.e., a portion in the vicinity of the outer surface of the stator core where the specific pressure becomes comparatively low. Therefore, measurement needs to be made at many portions. Further, it is likely that the actual measurement result is evaluated lower than the average specific pressure of the stator core with the result that the stator core is clamped with more force than required. Furthermore, in existing plant diagnosis, there is a case where even a problem-free machine is determined to be abnormal.

The present invention has been made to solve the above-mentioned problem, and an object thereof is to provide a stator core loosening diagnosis device and its diagnosis method capable of easily and quantitatively determining the clamping state of the entire stator core of a rotary electrical machine.

BRIEF SUMMARY OF THE INVENTION

The present invention achieves the above-mentioned object, and according to aspect of the present invention, there is provided a diagnosis device for diagnosing loosening of a stator core of a rotary electrical machine, the stator core being configured by laminating, in an axial direction, electromagnetic steel sheets on both or one of the surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis device being characterized by comprising: excitation means for vibrating the stator core in the radial direction thereof; vibration detection means for detecting the vibration of the stator core in the radial direction; means for frequency-analyzing an output signal of the vibration detection means that detects vibration generated in the stator core when the stator core is vibrated by the: excitation means so as to extract a measurement natural vibration mode of the stator core in a circular ring natural vibration mode; means for estimating a circular ring natural vibration mode of the stator core from shape data of the stator core; and means for determining a clamping state of the stator core by comparing the measurement natural vibration mode and a determination criterion obtained based on the estimated natural vibration mode.

According to another aspect of the present invention, there is provided a diagnosis device for diagnosing loosening of a stator core of a rotary electrical machine, the stator core being configured by laminating, in an axial direction, electromagnetic steel sheets on both or one of surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis device being characterized by comprising: excitation means for vibrating the stator core in a lateral direction thereof; vibration detection means for detecting the vibration of the stator core in the: excitation direction at a plurality of points arranged in axial direction of the stator core; means for frequency-analyzing an output signal of the vibration detection means that detects vibration generated in the stator core when the stator core is vibrated by the: excitation means so as to extract a measurement natural frequency of the stator core in a bending mode; means for estimating an estimated natural frequency of the stator core in the bending mode from shape data of the stator core; means for creating a determination value based on the estimated natural frequency; and determination means for determining the clamping state of the stator core by comparing the measurement natural frequency and determination value.

According to an aspect of the present invention, there is provided a diagnosis method for diagnosing the loosening of a stator core of a rotary electrical machine, the stator core being configured by laminating, in axial direction, electromagnetic steel sheets on both or one of surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis method being characterized by comprising: a: excitation step of vibrating the stator core in the radial direction thereof; a vibration detection step of detecting the vibration of the stator core when the stator core is vibrated in the: excitation step; a measurement natural vibration mode extraction step of frequency-analyzing an output signal of the vibration detection means so as to extract a measurement natural vibration mode of the stator core in a circular ring natural vibration mode; a natural vibration mode estimation step of estimating a circular ring natural vibration mode of the stator core from shape data of the stator core; and a determination step of determining a clamping state of the stator core by comparing the measurement natural vibration mode and a determination criterion obtained based on the estimated natural vibration mode.

According to another aspect of the present invention, there is provided a diagnosis method for diagnosing loosening of a stator core of a rotary electrical machine, the stator core being configured by laminating, in an axial direction, electromagnetic steel sheets on both or one of surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis method being characterized by comprising: a: excitation step of vibrating the stator core in a lateral direction thereof; a vibration detection step of detecting the vibration of the stator core at a plurality of points arranged in axial direction of the stator core when the stator core is vibrated in the: excitation step; a measurement natural frequency extraction step of frequency-analyzing an output signal detected in the vibration detection step so as to extract a measurement natural vibration mode of the stator core in a bending mode; a natural frequency estimation step of estimating an estimated natural frequency of the stator core in the bending mode from shape data of the stator core; and a determination step of determining the clamping state of the stator core by comparing the measurement natural vibration mode and determination value obtained based on the estimated natural frequency.

BRIEF DESCRIPTION OF THE DRAWINGS

The above and other features and advantages of the present invention will become apparent from the discussion hereinbelow of specific, illustrative embodiments thereof presented in conjunction with the accompanying drawings, in which.

DETAILED DESCRIPTION OF THE INVENTION

Embodiments of a diagnosis device for diagnosing loosening of a stator core of a rotary electrical machine and a loosening diagnosis method according to the present invention will be described below with reference to the accompanying drawings.

First Embodiment

Figure 1:
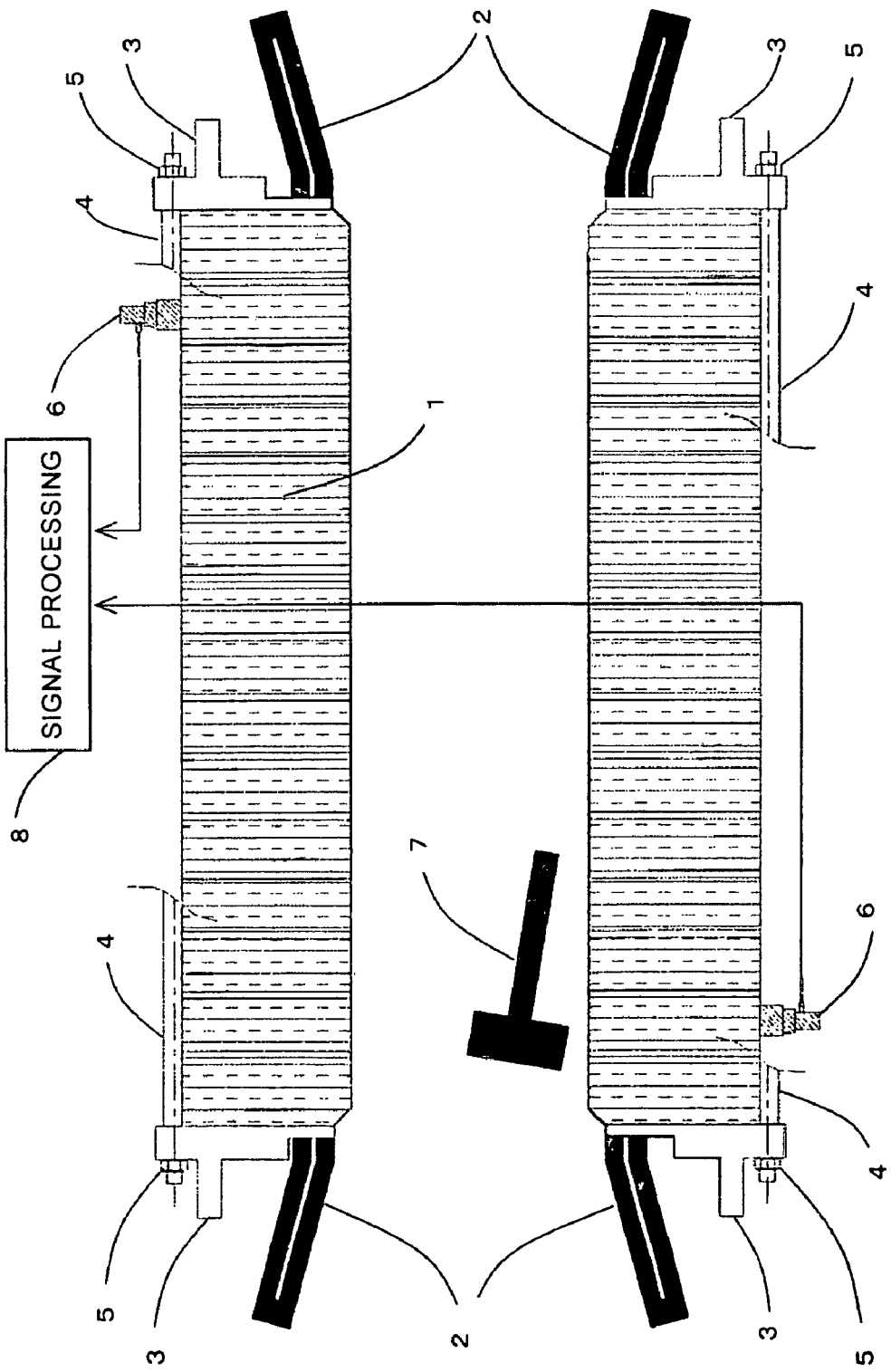
FIG. 1 is a longitudinal cross-sectional view schematically showing a first embodiment of a stator core of a rotary electrical machine and a stator core loosening diagnosis device.

A first embodiment of the present invention will be described with reference to FIGS. 1 and 2. In FIG. 1, a stator core 1 is configured by laminating thin electromagnetic steel sheets having, on its inner radial side, a space into which a coil 2 is inserted. The laminated electromagnetic steel sheets are clamped by retaining plates 3 provided at both axial direction end portions of the stator core 1. The clamping is achieved by screwing rib-nuts 5 into male screw portions located at both end portions of each of a plurality of rib bars 4 disposed on the outer radial side of the electromagnetic steel sheets. The coil 2 is connected outside the stator core 1.

A plurality of vibration sensors (vibration detection means) 6 are arranged on the outer radial side of the stator core 1 in the circumferential direction thereof and in the axial direction thereof including axial direction both end portions so as to detect vibration in the radial direction of the stator core 1. An excitation means 7 is, e.g., a hammer. The stator core 1 can be vibrated by striking the stator core 1 with the hammer 7 in the radial direction of the stator core 1. The output signals from the vibration sensors 6 are processed by a signal processing means 8.

Figure 2:
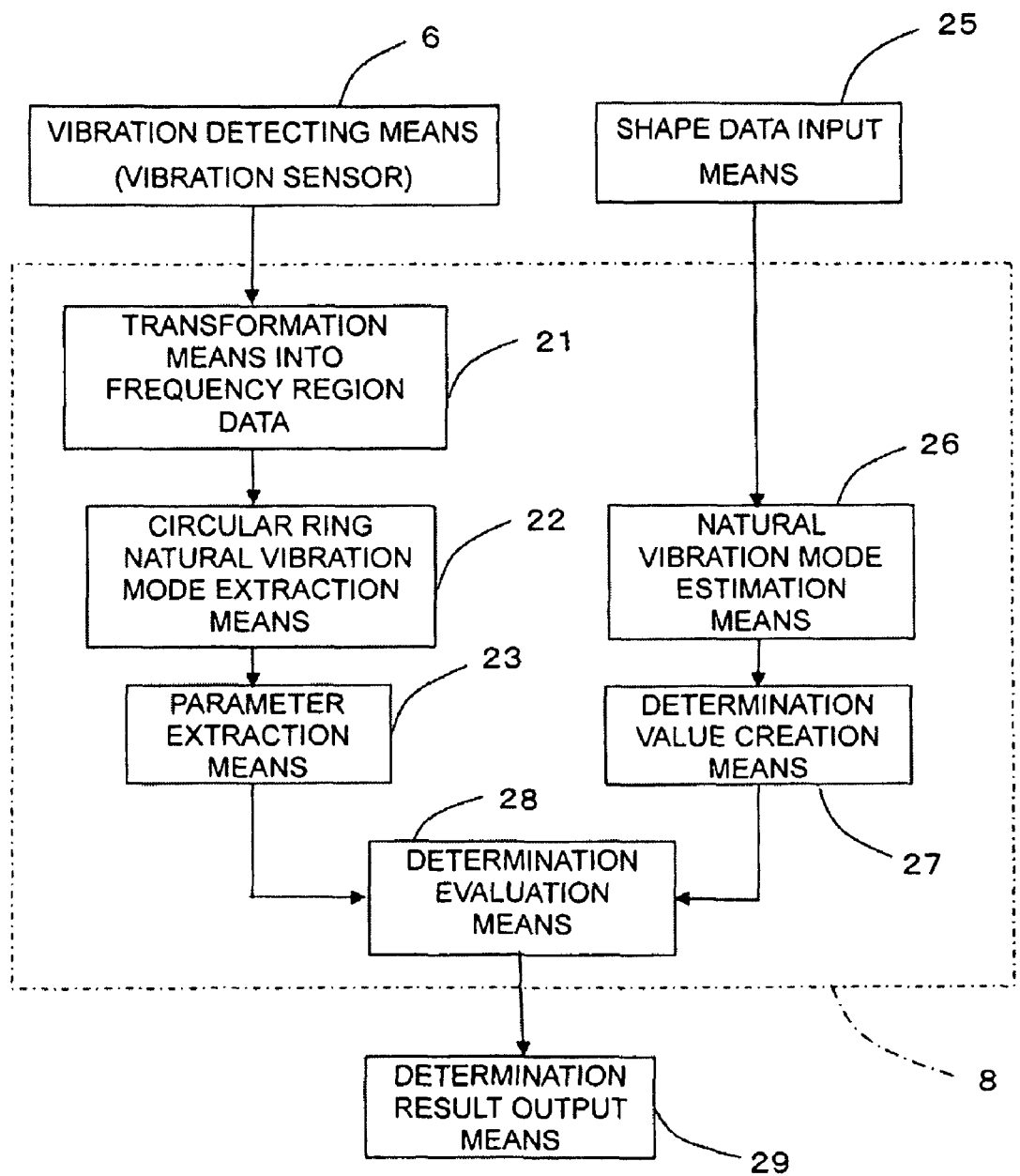
FIG. 2 is a block diagram showing a concrete configuration of a signal processing means of FIG. 1.

FIG. 2 shows a configuration example of the signal processing means 8. The output signals from the vibration sensors 6 are transformed into frequency range data by a transformation means 21. Then, circular ring mode vibration is extracted from the frequency range data by a circular ring natural vibration mode extraction means 22. Further, parameters are extracted from the circular ring mode vibration by a parameter extraction means 23.

Meanwhile, shape data is input by a shape data input means 25, and, based on the shape data, a natural vibration mode is estimated by a natural vibration mode estimation means 26. Further, based on the estimated natural vibration mode, a determination value is created by a determination value creation means 27. Finally, based on the parameter extracted by the parameter extraction means 23 and determination value created by the determination value creation means 27, determination evaluation is made by a determination evaluation means 28. The determination evaluation result is output by a determination result output means 29.

When the stator core 1 is struck using the excitation means 7 in the first embodiment having the configuration described above, the stator core 1 vibrates in a natural vibration mode of a circular ring mode. FIGS. 3 to 7 are views each conceptually showing deformation of the stator core 1 when the stator core 1 vibrates in a natural vibration mode of a circular ring mode. The deformation in the above examples is calculated by numerical analysis using a finite element method (FEM). It should be noted that deformation in the radial direction is exaggerated in the examples shown in FIGS. 3 to 7. Reference numeral 70 in FIGS. 3 to 7 denotes a slot (insertion space) into which the coil 2 is inserted. The slot is formed on the inner radial side of the stator core 1 and extends in the axial direction thereof.

Figure 3:
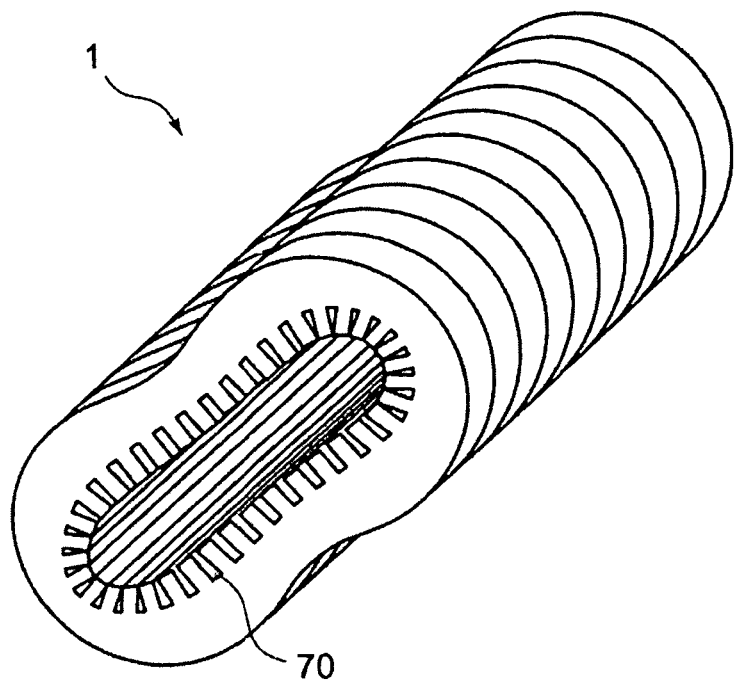
FIG. 3 is a conceptual view of the natural vibration mode of a stator core of a typical rotary electrical machine vibrating in a second-order circular ring axial direction in-phase mode.
Figure 4:
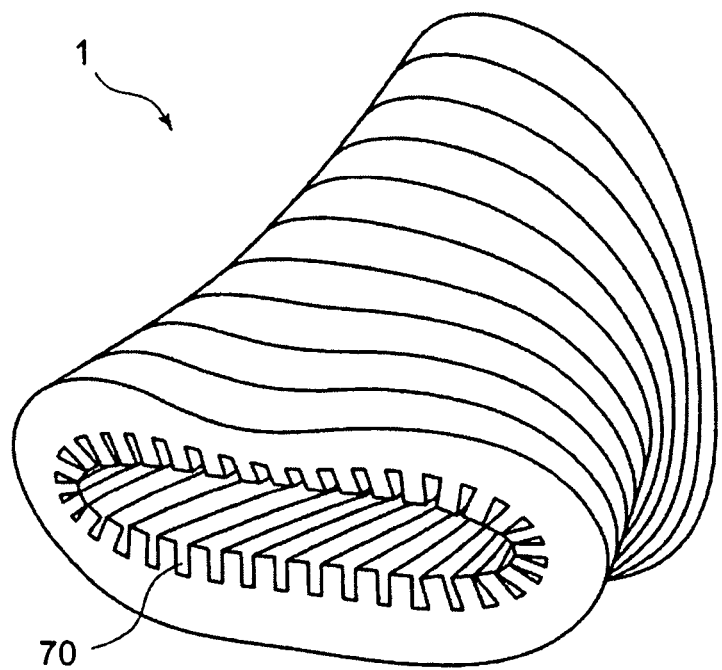
FIG. 4 is a conceptual view of the natural vibration mode of a stator core of a typical rotary electrical machine vibrating in a second-order circular ring axial direction out-of-phase mode.
Figure 5:
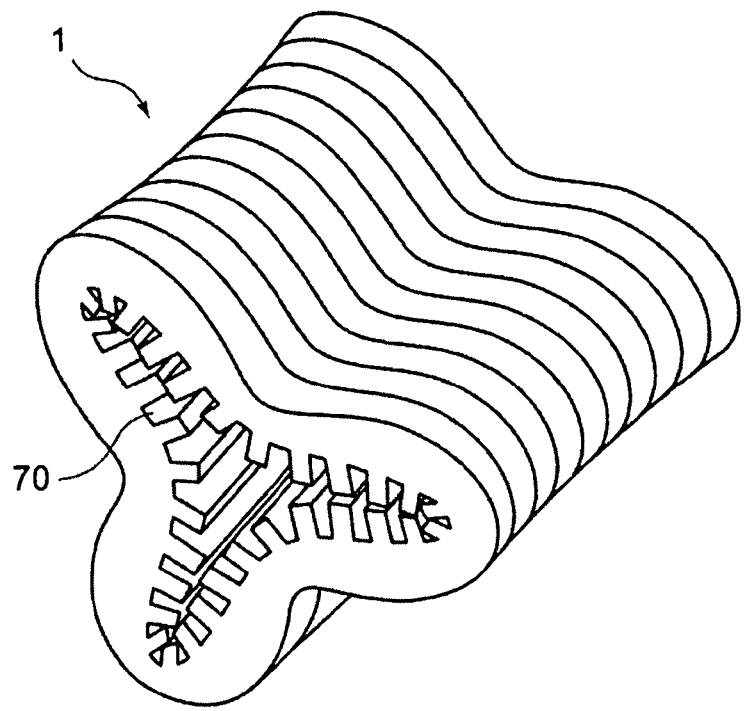
FIG. 5 is a conceptual view of the natural vibration mode of a stator core of a typical rotary electrical machine vibrating in a third-order circular ring axial direction in-phase mode.
Figure 6:
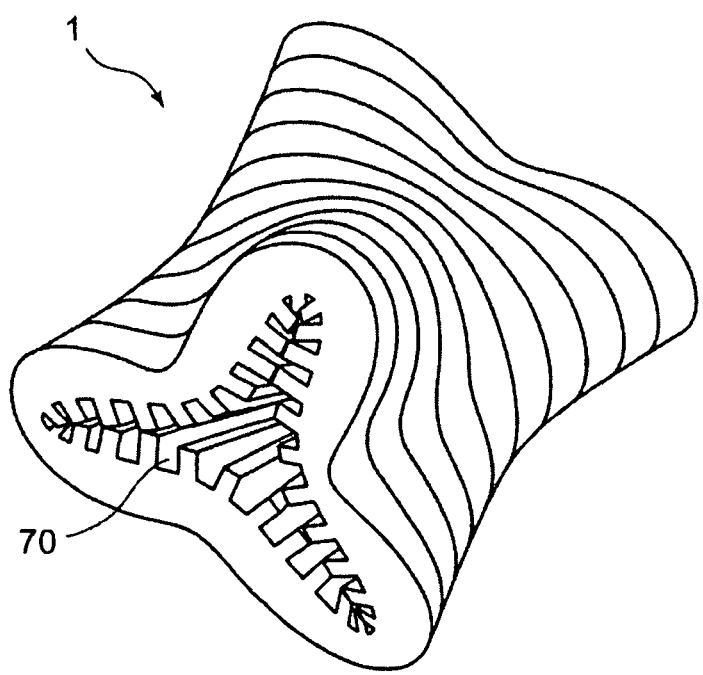
FIG. 6 is a conceptual view of the natural vibration mode of a stator core of a typical rotary electrical machine vibrating in a third-order circular ring axial direction out-of-phase mode.
Figure 7:
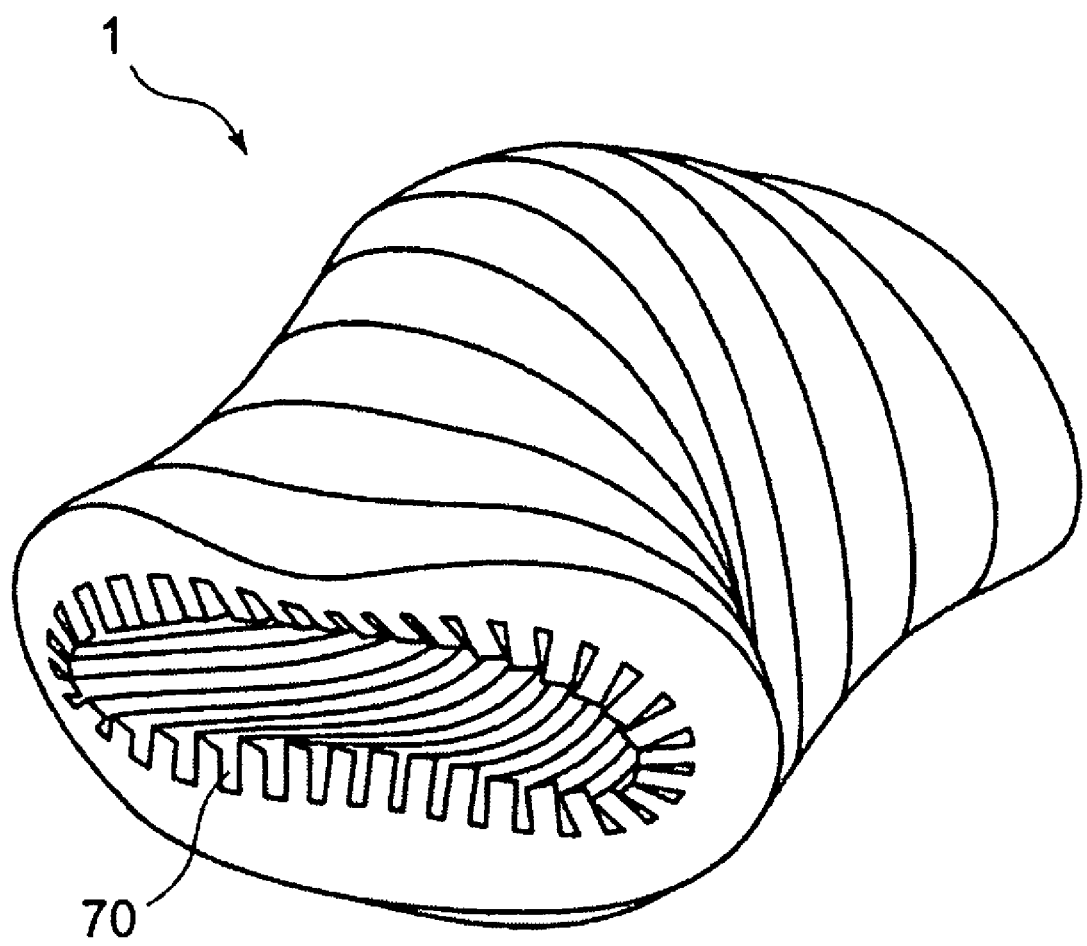
FIG. 7 is a conceptual view of the natural vibration mode of a stator core of a typical rotary electrical machine vibrating in a second-order circular ring axial direction U-curve mode.

FIG. 3 shows a deformation state of the stator core 1 vibrating in a second-order circular ring (ellipse) axial direction in-phase mode, FIG. 4 shows a deformation state of the stator core 1 vibrating in a second-order circular ring (ellipse) axial direction out-of-phase mode, FIG. 5 shows a deformation state of the stator core 1 vibrating in a third-order circular ring (trefoil shape) axial direction in-phase mode, FIG. 6 shows a deformation state of the stator core 1 vibrating in a third-order circular ring (trefoil shape) axial direction out-of-phase mode, and FIG. 7 shows a deformation state of the stator core 1 vibrating in a second-order circular ring (ellipse) axial direction U-curve mode.

Although not shown, the circular ring vibration mode may also include an axial direction S-curve mode, axial direction M (W)-curve mode, or the like.

In the present embodiment, since the vibration sensors 6 are attached to positions at which the vibration of a target vibration mode can be measured, they can detect the vibration waveform of a target vibration mode. Vibration signals detected by the vibration sensors 6 are sent to the signal processing means 8 and are then Fourier-transformed by the transformation means 21 into frequency range data in the signal processing means 8. The frequency range data is input to the circular ring natural vibration mode extraction means 22 so as to cause the circular ring natural vibration mode extraction means 22 to extract the respective modes of the circular ring vibration based on the amplitudes measured by the plurality of vibration sensors 6 arranged on the stator core 1, phase relationship therebetween, and feature of the deformation of the stator core 1 exemplified in FIGS. 3 to 7.

Then, the parameter extraction means 23 transforms the circular ring vibration mode extracted by the circular ring natural vibration mode extraction means 22 into a parameter (e.g., natural frequency, ratio between a plurality of natural frequencies, damping ratio of natural oscillation, amplitude ratio, or transfer function) correlated to the residual specific pressure of the stator core 1.

Figure 8:
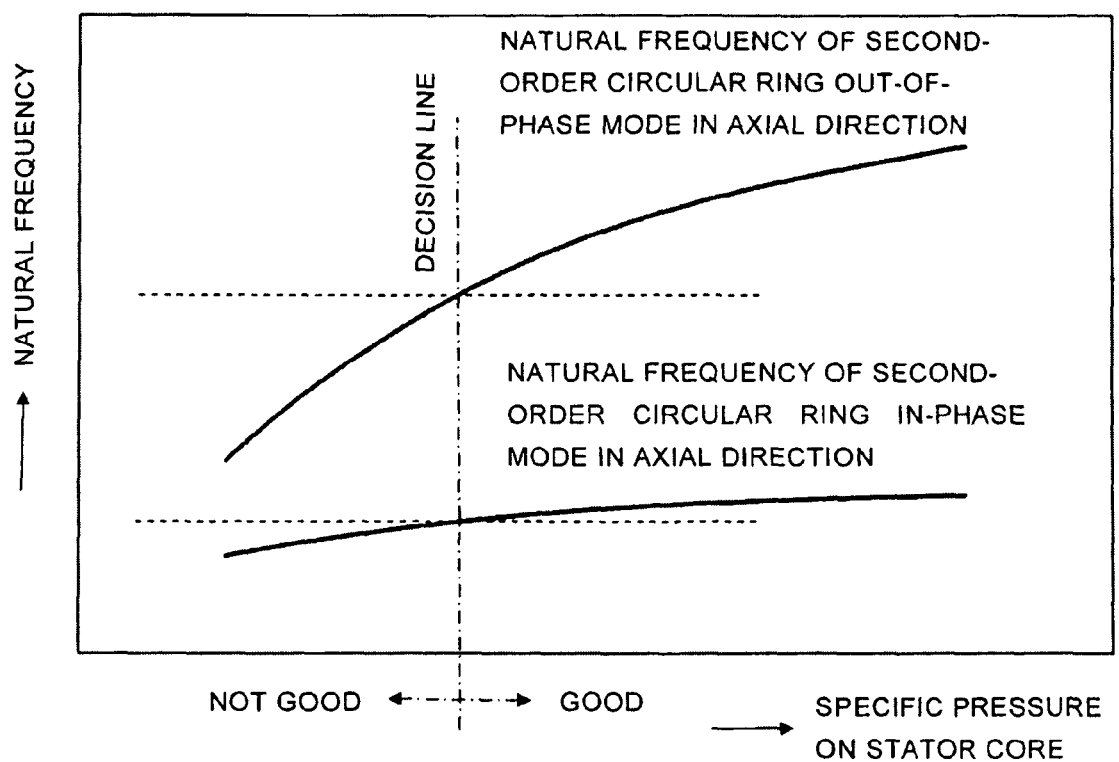
FIG. 8 is a graph for explaining signal processing performed in the first embodiment of the stator core loosening diagnosis device according to the present invention, which shows a concept of a relationship between the stator core specific pressure and natural frequency in the circular ring mode.
Figure 9:
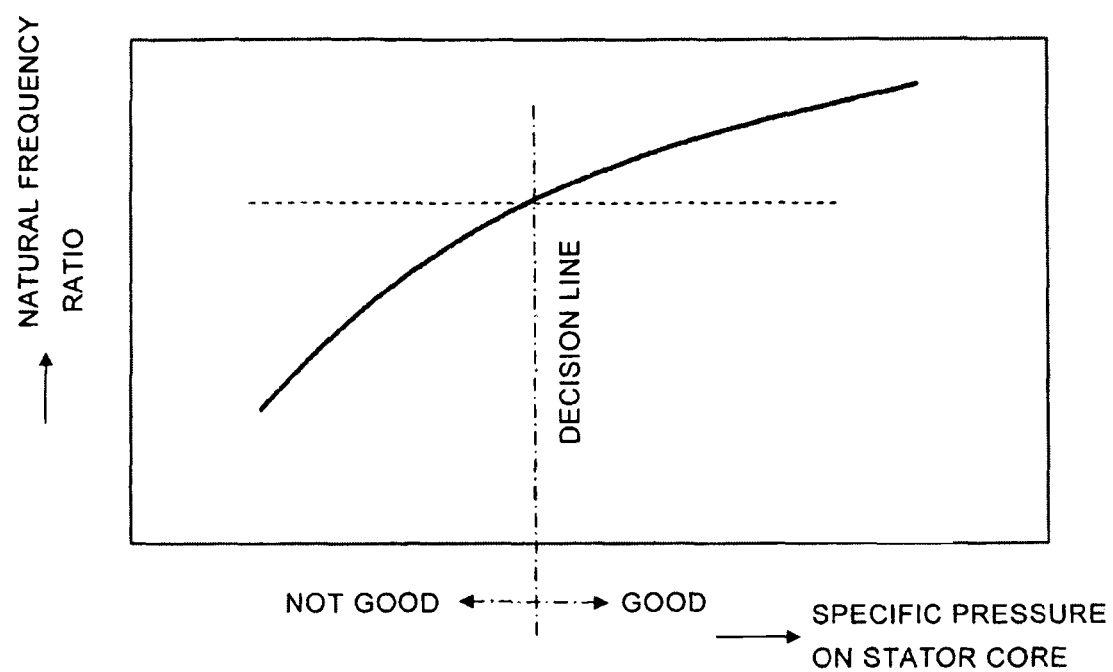
FIG. 9 is a graph for explaining signal processing performed in the first embodiment of the stator core loosening diagnosis device according to the present invention, which shows a concept of a relationship between the stator core specific pressure and a ratio between the natural frequencies in the axial direction in-phase mode and axial direction out-of-phase mode.
Figure 11:
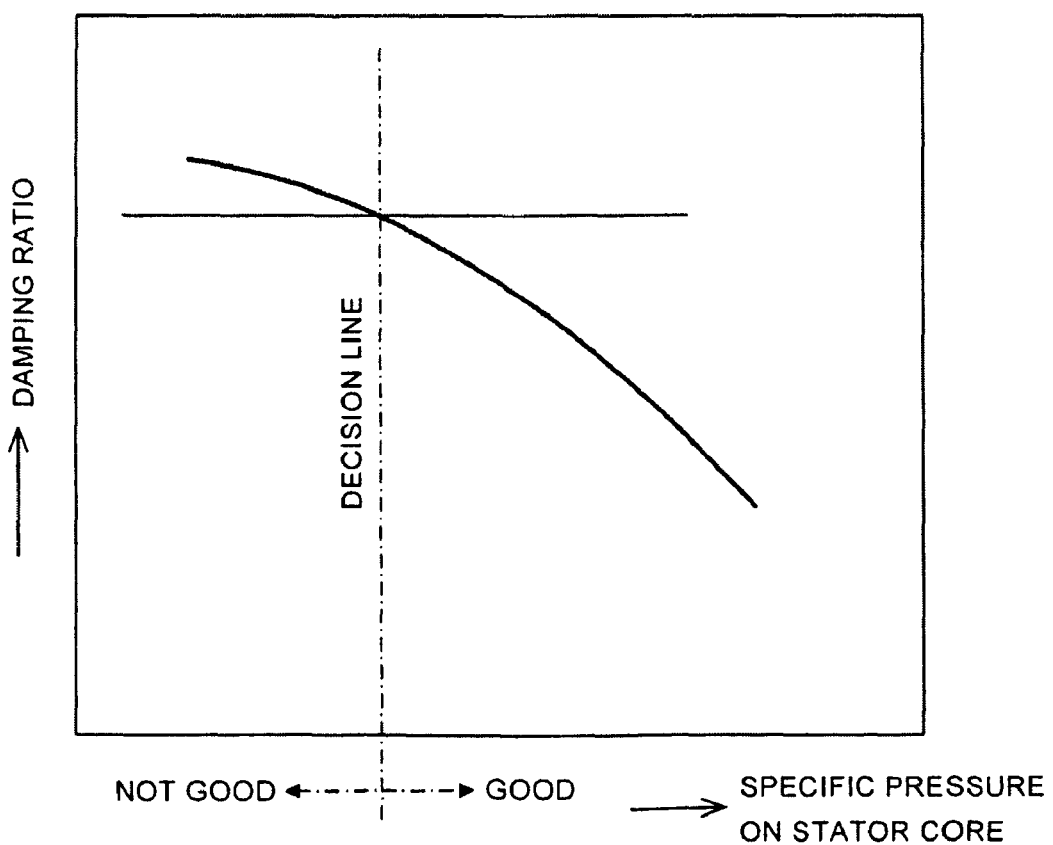
FIG. 11 is a graph for explaining signal processing performed in the first embodiment of the stator core loosening diagnosis device according to the present invention, which shows a concept of a relationship between the stator core specific pressure and damping ratio in a circular ring natural vibration mode.

Meanwhile, the natural vibration mode estimation means 26 of the signal processing means 8 estimates a natural vibration mode of the stator core 1 in the circular ring mode by numerical analysis using a finite element method based on dimension data of the stator core 1 of a target rotary electrical machine. Then, the estimation result is input to the determination value creation means 27 so as to create a determination value corresponding to the parameter of vibration which is the output of the signal processing means. The relationship between the stator core specific pressure and each parameter is roughly as shown in FIG. 8, 9, or 11. Then, the parameter value obtained by actual measurement and determination value calculated from the dimension data are compared so as to be output as the determination result.

Figure 10:
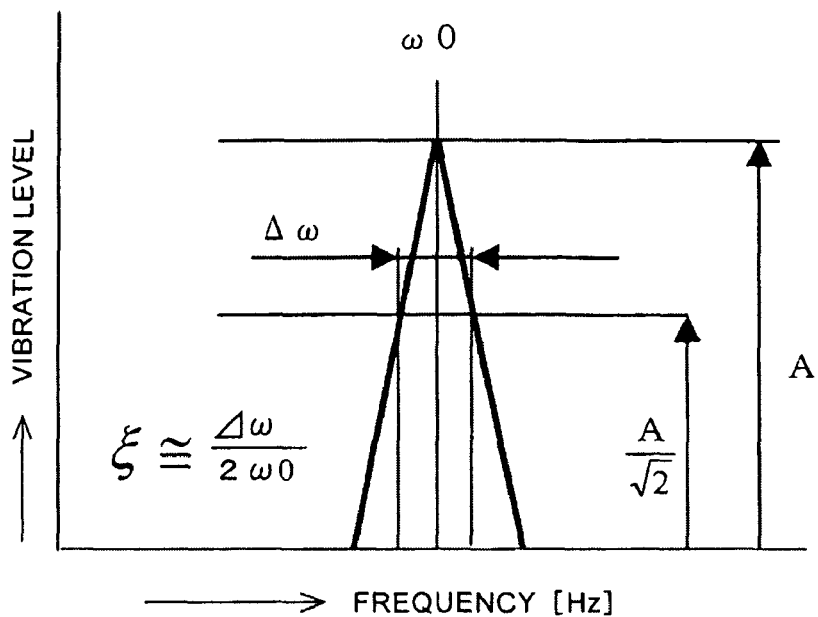
FIG. 10 is a graph for explaining a typical method for calculating a damping ratio from a result obtained by analyzing the frequency of vibration data, in which frequency is plotted on the horizontal axis and vibration level is plotted on the longitudinal axis.

The damping ratio can be calculated from the frequency range data of vibration by a method shown in FIG. 10. In FIG. 10, the horizontal axis is frequency [Hz], and longitudinal axis is vibration level. Further, ω0 is the angular speed of natural oscillation. Assuming that the natural frequency is F0, ω0=2πF0 is satisfied. Further, Δω is the width of the angular speed obtained when the amplitude is 1/√2 of the amplitude obtained when the angular speed is ω0. ζ is damping ratio.

ζ is represented by Δω/2ω0.

As described above, the residual specific pressure of the stator core can quantitatively grasped by measuring the vibration of the circular ring mode of the stator core 1.

According to the present invention, by comparing a determination value obtained from the dimension data of a machine to be diagnosed and parameter obtained from the actual measurement data, the current residual specific pressure can be quantitatively determined from each parameter corresponding to the natural vibration mode of the stator core in the circular ring mode. As a result, it is possible to determine and diagnose the loosening state of the stator core irrespective of the skill or ability of the inspector.

Second Embodiment

Figure 12:
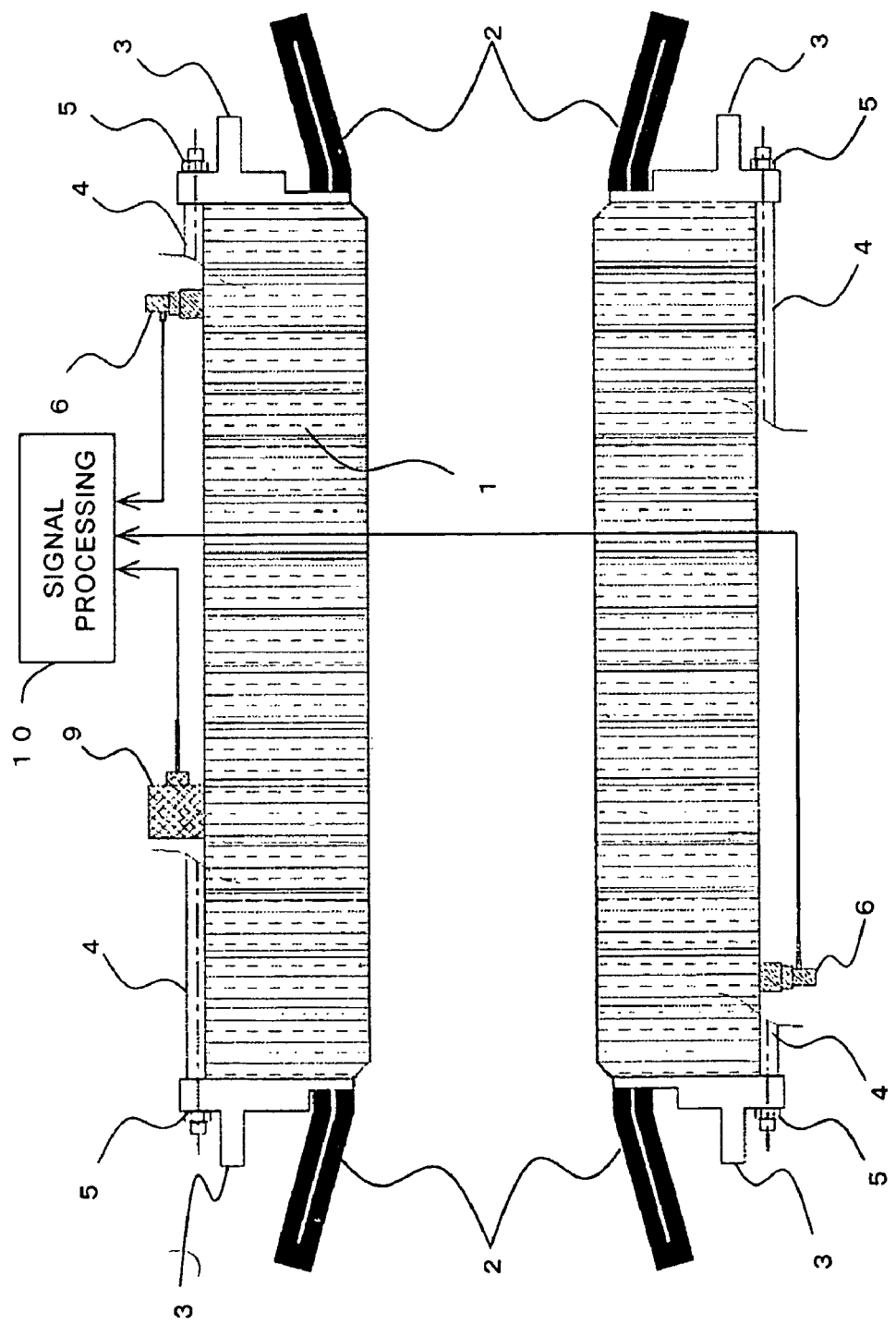
FIG. 12 is a longitudinal cross-sectional view schematically showing a second embodiment of a stator core of a rotary electrical machine and a stator core loosening diagnosis device.
Figure 13:
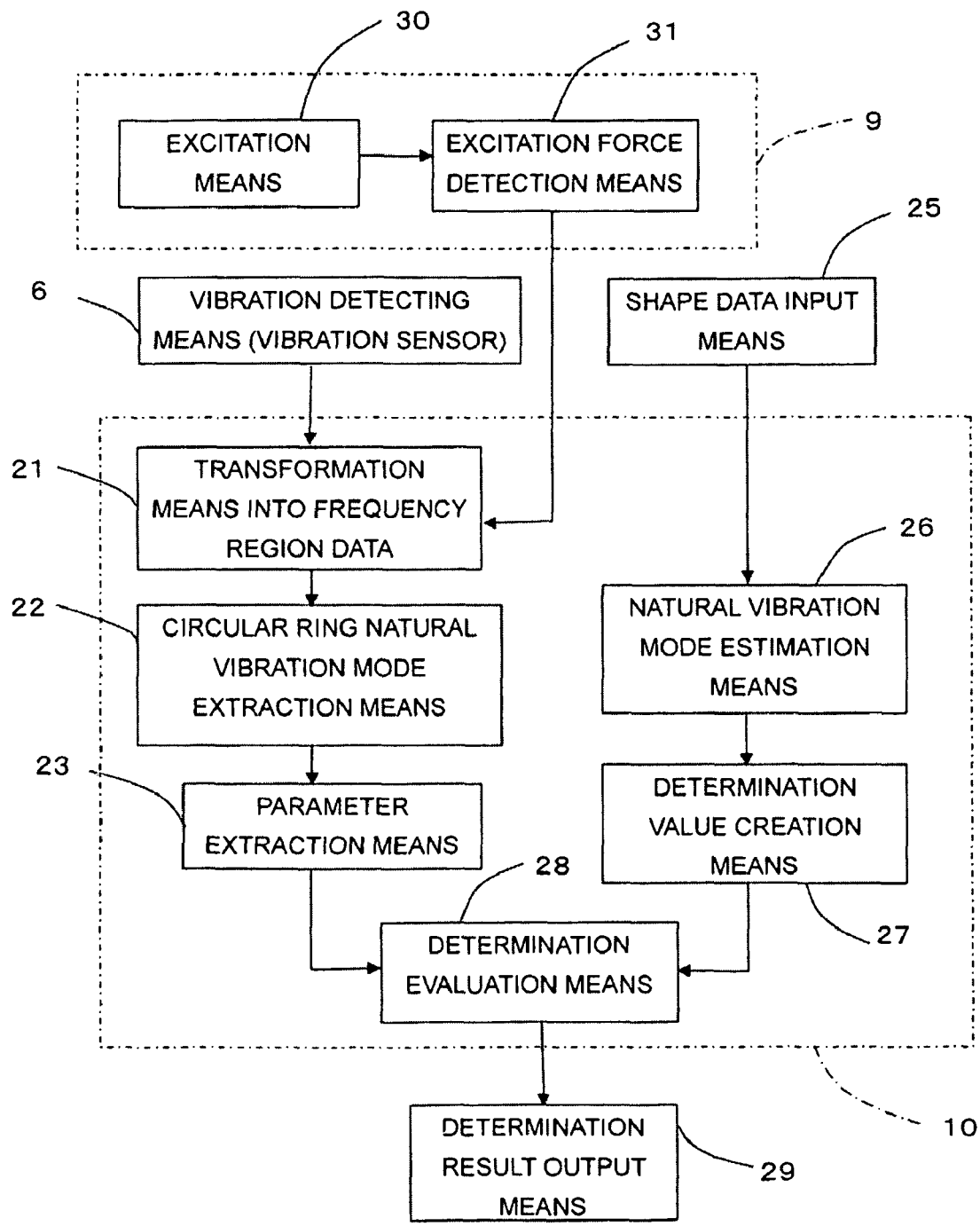
FIG. 13 is a block diagram showing a concrete configuration such as a signal processing means and: excitation/excitation force detection means shown in FIG. 12.

A second embodiment of the stator core loosening diagnosis device according to the present invention and rotary electrical machine incorporating the diagnosis device will be described below with reference to FIGS. 12 and 13. In FIGS. 12 and 13, the same reference numerals as those in the first embodiment denote the same or corresponding parts as those in the first embodiment, and the descriptions thereof will be omitted here.

An excitation/excitation force detection means 9, which is constituted by a: excitation means 30 and a vibration-applying force detection means 31, is rigidly fixed to the outer diameter surface of the stator core 1 and vibrates the stator core 1 in the radial direction thereof. The excitation/excitation force detection means 9 is vibrated by a single sine wave, a waveform obtained by superimposing a plurality of sine waves, a sine wave sweeping over a certain frequency range, a triangular wave, a rectangular wave, or a random wave.

The vibration applying force of the excitation means 30 is detected by the vibration-applying force detection means 31 and is sent to a signal processing means 10 together with the output signal of the plurality of vibration sensors 6 that are arranged on the stator core 1 and detect the vibration of the stator core 1 in the radial direction thereof.

In the stator core loosening diagnosis device according to the second embodiment having the configuration described above, vibration waveform data of the circular ring mode detected by the vibration sensor 6 attached in a permanent manner to the inside of a rotary electrical machine and vibration applying force waveform data detected by the vibration-applying force detection means 31 also attached in a permanent manner to the inside of the rotary electrical machine are both transformed into frequency range data by the transformation means 21 provided in the signal processing means 10. Further, the obtained vibration data is then transformed into a transfer function using the vibration applying force as a reference, followed by extraction of the vibration of the circular mode by the circular ring natural vibration mode extraction means 22.

As a result, the specific pressure of the stator core can accurately be grasped without being influenced by the magnitude of the excitation force. Further, since the excitation/excitation force detection means 9 and vibration sensor 6 are attached to the inside of the rotary electrical machines in a permanent manner, the residual specific pressure of the stator core 1 can be monitored constantly or diagnosed periodically without a need of disassembling the rotary electrical machine. Further, by vibrating the excitation means 30 at the natural frequency in the previously calculated circular ring mode, determination can be made with high sensitivity in the case where the amplitude or amplitude ratio is used as a parameter. Further, by superimposing a plurality of natural frequencies so as to vibrate the stator core 1, a plurality of natural frequencies can be excited with high sensitivity. Furthermore, by exciting vibration using a random wave, or sweeping wave, the natural frequency in a target circular ring mode can be excited even if slightly deviated, enabling the vibration mode to be clearly grasped.

Since the excitation/excitation force detection means 9 and vibration sensor 6 are attached to the stator core 1 of the rotary electrical machine in a permanent manner so as not to interfere with the original function of the rotary electrical machine, the residual specific pressure of the stator core 1 can be monitored constantly or diagnosed periodically during operation time without a need of disassembling the rotary electrical machine. Therefore, it is possible to prevent a failure of the stator core 1, as well as to easily diagnose the loosening of the stator core 1. Further, by detecting the vibration applying force to calculate a transfer function using the vibration applying force as a reference, it is possible to remove the influence due to the magnitude of the vibration applying force, thereby improving reliability of a diagnosis result. Further, by setting a excitation signal for vibrating the stator core 1 in various forms as described above, determination sensitivity can be increased, or determination can be made in a variety of modes.

Third Embodiment

Figure 14:
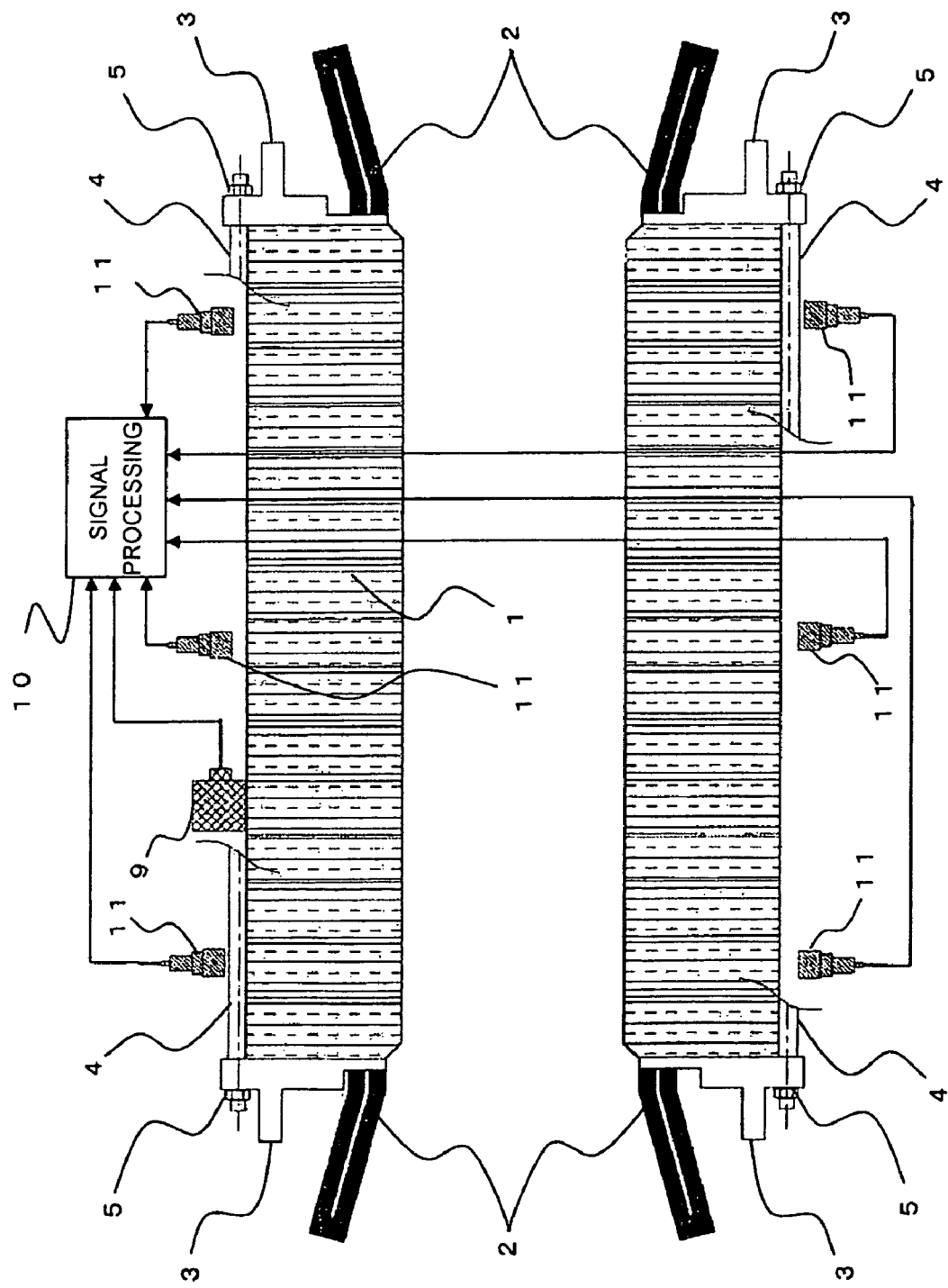
FIG. 14 is a longitudinal cross-sectional view schematically showing a third embodiment of a stator core of a rotary electrical machine and a stator core loosening diagnosis device.

A third embodiment of the stator core loosening diagnosis device according to the present invention and rotary electrical machine incorporating the diagnosis device will be described below with reference to FIG. 14. In FIG. 14, the same reference numerals as those in the first or second embodiments denote the same or corresponding parts as those in the first or second embodiments, and the descriptions thereof will be omitted here. In FIG. 14, an acoustic or displacement sensor 11 is fixedly attached to the outer surface of the stator core 1 of the rotary electrical machine with a space kept therebetween and detects acoustic wave or displacement generated when the stator core 1 vibrates. The signal detected by the acoustic or displacement sensor 11 is sent to the signal processing means 10.

In the stator core loosening diagnosis device according to the third embodiment having the configuration described above, vibration of the natural vibration mode of the circular ring mode of the stator core 1 is detected by the acoustic or displacement sensor 11 and is then sent to the signal processing means 10. Afterward, the same signal processing as that according to the first or second embodiment is performed to determine the residual specific pressure of the stator core to thereby diagnose the loosening of the stator core 1. As in the case of using the vibration sensor 6, by using the acoustic or displacement sensor 11, it is possible to detect the vibration of the natural vibration mode of the stator core 1 in the circular ring mode.

As described above, in the third embodiment, the acoustic or displacement sensor 11 is used in place of the vibration sensor 6 to detect the vibration of the natural vibration mode of the stator core 1 in the circular ring mode. The use of the acoustic or displacement sensor 11 of non-contact type eliminates the need to provide electrical isolation and facilitates the change of the attachment position of the acoustic or displacement sensor 11.

Fourth Embodiment

Figure 15:
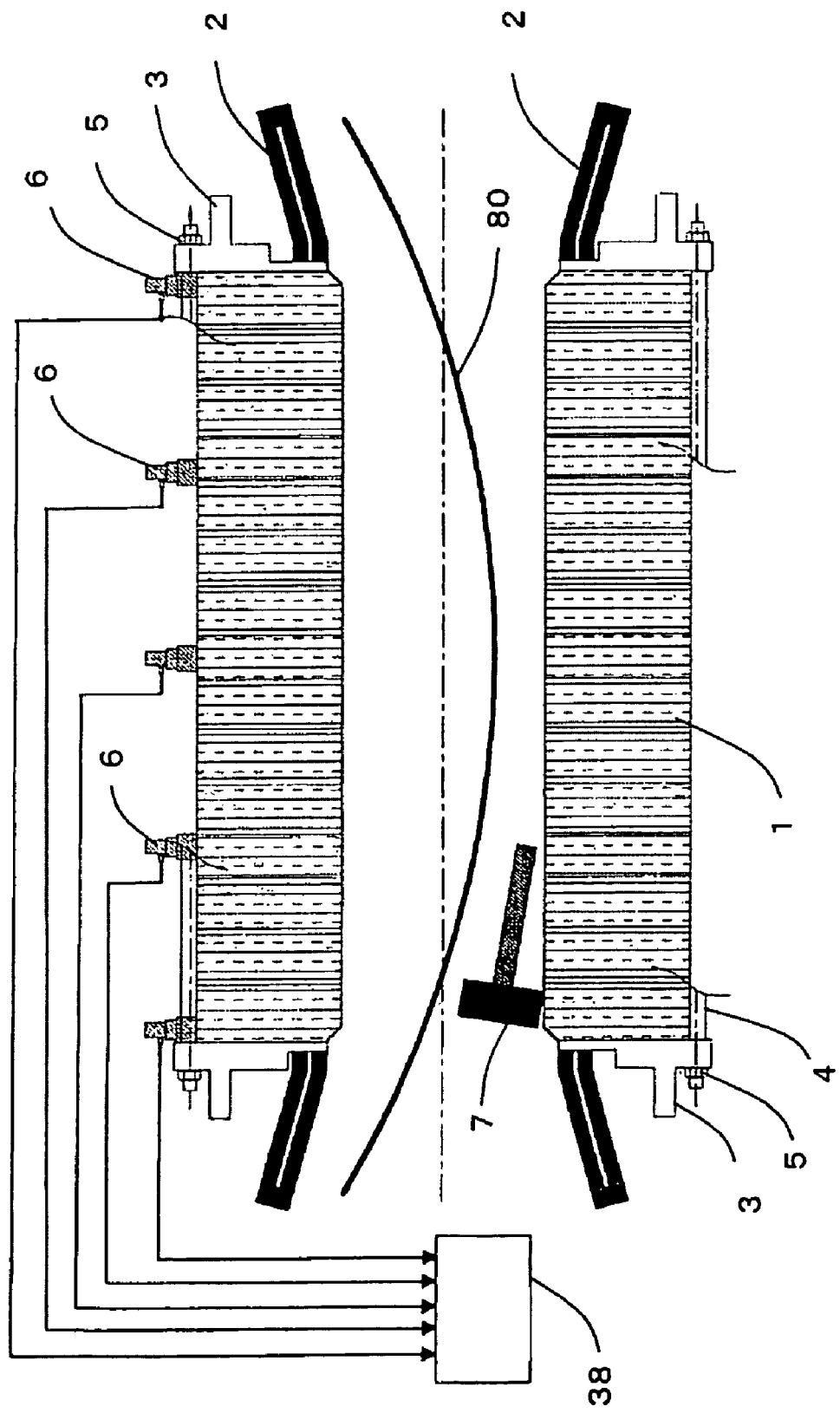
FIG. 15 is a longitudinal cross-sectional view schematically showing a fourth embodiment of a stator core of a rotary electrical machine and a stator core loosening diagnosis device.
Figure 16:
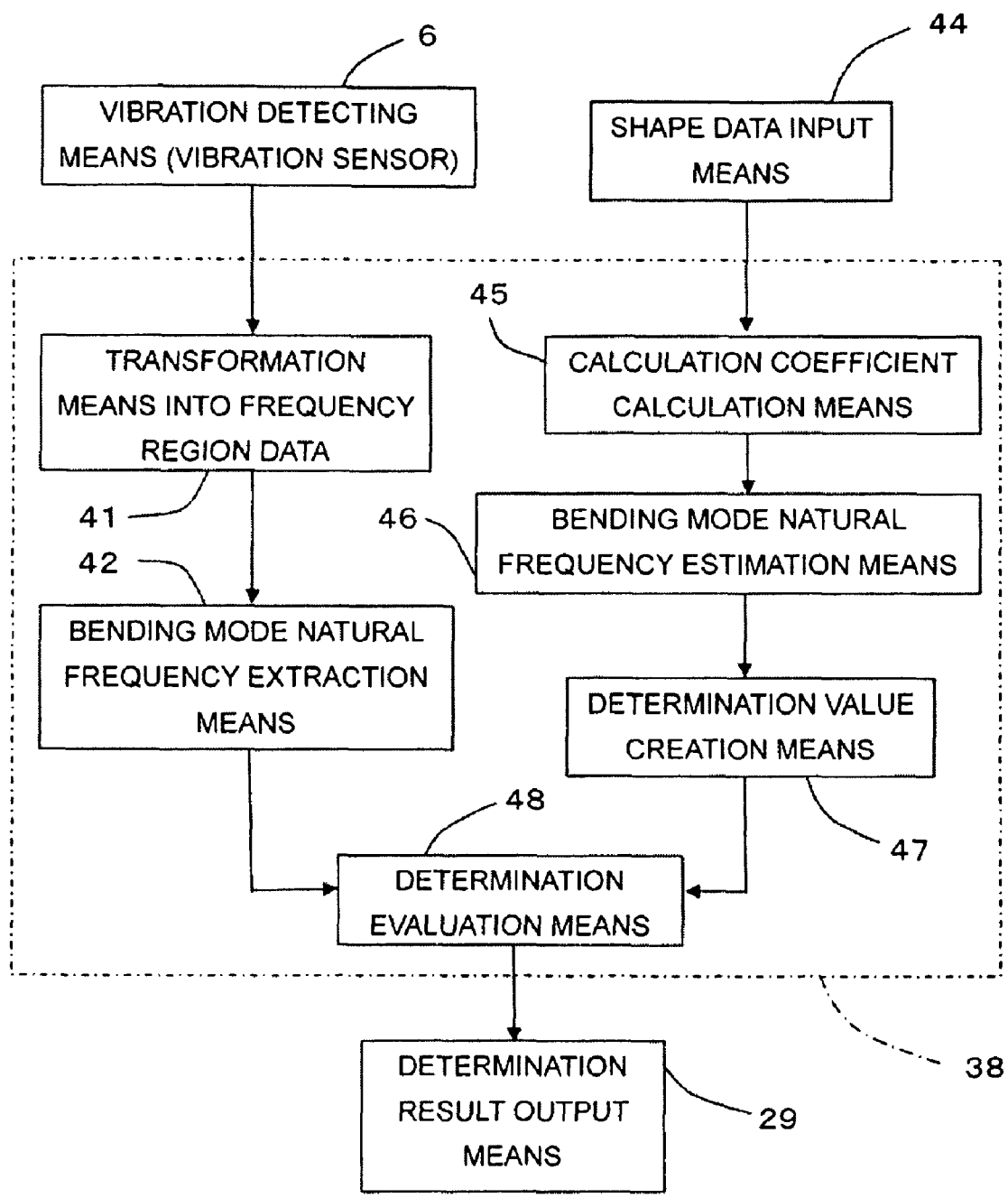
FIG. 16 is a block diagram showing a concrete configuration of a signal processing means shown in FIG. 15.

A fourth embodiment of the stator core loosening diagnosis device according to the present invention and rotary electrical machine incorporating the diagnosis device will be described below with reference to FIGS. 15 and 16. In FIGS. 15 and 16, the same reference numerals as those in the first embodiment denote the same or corresponding parts as those in the first embodiment, and the descriptions thereof will be omitted here. Although the first to third embodiments focus on the circular ring vibration mode of the stator core of the rotary electrical machine, the present embodiment focuses on the bending mode of the stator core.

As shown in FIG. 15, in the present embodiment, a plurality of vibration sensors 6 are attached to the outer radial side of the stator core 1 in the axial direction thereof so as to detect the vibration of the stator core 1 in the excitation direction. Detection signals from the vibration sensors 6 are sent to a signal processing means 38 for predetermined signal processing.

As shown in FIG. 16, the signal processing means 38 includes a transformation means 41 into frequency range data, a bending mode natural frequency extraction means 42, a calculation coefficient calculation means 45, a bending mode natural frequency estimation means 46, a determination value creation means 47, and a determination evaluation means 48. The output signals from the vibration sensors 6 are transformed into frequency range data by the transformation means 41. Then, the natural frequency in the bending mode is extracted by the bending mode natural frequency extraction means 42.

Meanwhile, the shape data is input by a shape data input means 44 and, based on the shape data, a calculation coefficient is calculated by the calculation coefficient calculation means 45. Further, based on the calculation coefficient, an estimated natural frequency of the bending vibration is estimated by the bending mode natural frequency estimation means 46. Then, based on the estimated natural vibration mode of the bending vibration, a determination value is created by the determination value creation means 47. Finally, based on the determination value and natural frequency extracted by the bending mode natural frequency extraction means 42, determination evaluation is made by the determination evaluation means 48. The determination evaluation result is output by a determination result output means 29.

Figure 17:
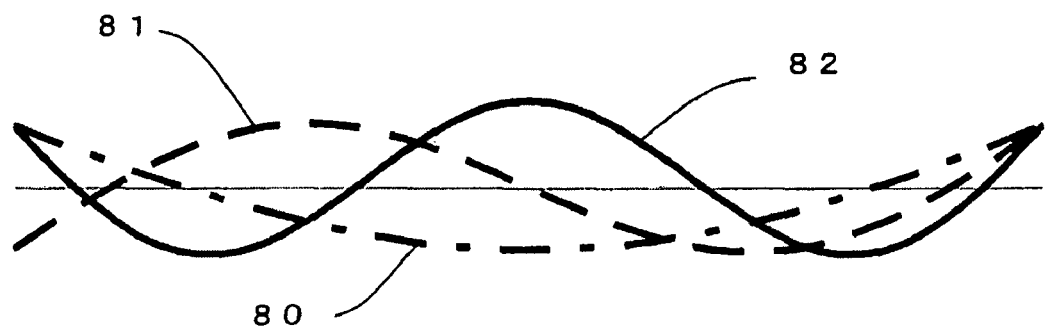
FIG. 17 is a view schematically showing a vibration mode of the bending vibration of a beam serving as a determination criterion in the fourth embodiment of the stator core of a rotary electrical machine and stator core loosening diagnosis device according to the present invention.

When the stator core 1 is struck using the excitation means 7 in the fourth embodiment having the configuration described above, the stator core 1 vibrates at a natural frequency in the bending mode, e.g., in a bending mode 80, that is, the stator core 1 vibrates in a U-like shape along the axial direction as shown in FIG. 15. FIG. 17 is a view schematically showing deformation of the stator core 1 when the stator core 1 vibrates at a natural frequency of the bending vibration. The deformation shown in FIG. 17 is calculated by numerical analysis. As shown in FIG. 17, the bending mode mainly includes vibration modes of first-order, second-order, and third-order natural frequency. In a vibration mode 80 of the first-order natural frequency, a target object is deformed into a U-like shape. In a vibration mode 81 of the second-order natural frequency, a target object is deformed into an S-like shape. In a vibration mode 82 of the third-order natural frequency, a target object is deformed into a W-like (or M-like) shape.

A natural frequency F of the bending mode of a typical beam can be calculated by the following expression (1).

$$F=\{\lambda 2/(2\pi L2)\}\sqrt{\{E \cdot Ig/\gamma \cdot A\}} \quad (1)$$

where:
F: Natural frequency of a bar in bending vibration
λ: Vibration coefficient corresponding to order of mode first-order: 4.730, second-order: 7.853, third-order: 10.996
L: Bar length
E: Young's modulus of material of a bar (E=k×P)
P: Stator core specific pressure
k: coefficient of Young's modulus and stator core specific pressure
I: Moment of inertia of area of bar
γ: Mass density
A: Crosssection area
g: Acceleration of gravity Since the vibration sensors 6 are arranged in the axial direction so that the vibration of a target vibration mode can be measured, they can detect the vibration waveform of a target vibration mode. Vibration signals detected by the vibration sensors 6 are sent to the signal processing means 38 and are then Fourier-transformed by the transformation means 41 in the signal processing means 38 into frequency range data. The frequency range data is input to the bending mode natural frequency extraction means 42 so as to cause bending mode natural frequency extraction means 42 to extract respective vibration modes of the bending vibration based on the amplitudes measured by the plurality of vibration sensors 6 arranged on the stator core 1, phase relationship therebetween, and feature of the deformation of the stator core 1 exemplified in FIG. 18. Thus, one or more natural frequencies of the bending vibration are extracted.

Meanwhile, in the signal processing means 38, dimension and shape data is input from the shape data input means 44 of the stator core 1 of a target rotary electrical machine, shape correction coefficient k1 and support condition correction coefficient k2 are calculated in the calculation coefficient calculation means 45, and natural frequency in each bending mode is calculated from the previously obtained relationship between the stator core specific pressure and equivalent Young's modulus E by the bending mode natural frequency estimation means 46. Finally, a determination value for determining the specific pressure is set based on the past results by the determination value creation means 47.

The shape correction coefficient k1 depends on the support conditions such as the number of supporting points, positions thereof, and spring constant.

The support condition correction coefficient k2 depends on the ratio between the inner and the outer diameters of the stator core 1 and the ratio between the length in the axial direction and the outer (or inner) diameter of the stator core 1.

The Young's modulus E in the above expression (1) can be represented as E=k×P. Actually, however, the following expression (2) obtained by taking the shape correction coefficient k1 and support condition correction coefficient k2 into consideration is used to calculate the natural frequency F.

$$F=\{k1 \cdot k2 \cdot \lambda 2/(2\pi L2)\}\sqrt{\{E \cdot Ig/\gamma \cdot A\}} \quad (2)$$

where k1 is shape correction coefficient, and k2 is support condition correction coefficient.

Figure 18:
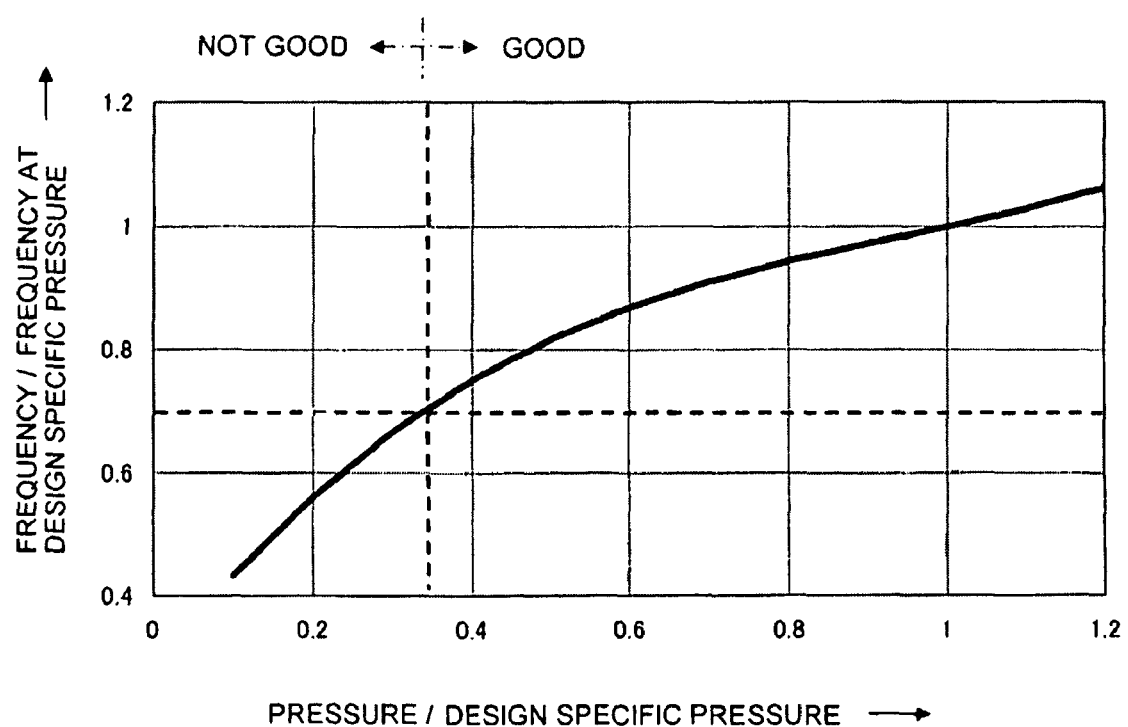
FIG. 18 is a graph for explaining signal processing performed in the fourth embodiment of the stator core loosening diagnosis device according to the present invention, which shows a concept of a relationship between the stator core specific pressure and natural frequency using a value relative to each design value thereof.

The determination value calculated by the determination value creation means 47 is roughly as shown in FIG. 18. Then, the actual measurement value of the natural frequency obtained by the bending mode natural frequency extraction means 42 and determination value shown in FIG. 18 which is the output of the determination value creation means 47 are compared with each other by the determination evaluation means 48 to determine the level of the clamping state of the stator core 1. Afterward, the determination result is output by the determination result output means 29.

Thus, it is possible to quantitatively grasp the clamping specific pressure of the stator core 1 by measuring the natural vibration mode of the stator core 1 in the bending mode.

According to the present embodiment, by comparing the determination value obtained based on the dimension data of a machine to be diagnosed and actual measurement value of the vibration, it is possible to quantitatively determine the current clamping specific pressure of the stator core from the natural frequency of the stator core in the bending mode. Therefore, the clamping state of the stator core, in other words, loosening state of the stator core can accurately be determined and diagnosed irrespective of the skill or ability of the inspector. Further, the determination value serving as a criterion can be obtained by a simple calculation at the hand calculation or table calculation level, thus eliminating the need to perform numerical analysis such as a finite element method. This results in elimination of the need to use a high-functional computer. Further, the time for performing analysis as well as high-level technique for performing the analysis is not required. Therefore, anyone can easily perform determination of the stator core specific pressure and diagnosis of the loosening of the stator core in a short period of time. Especially, an existing machine can be diagnosed where it is installed.

Fifth Embodiment

Figure 19:
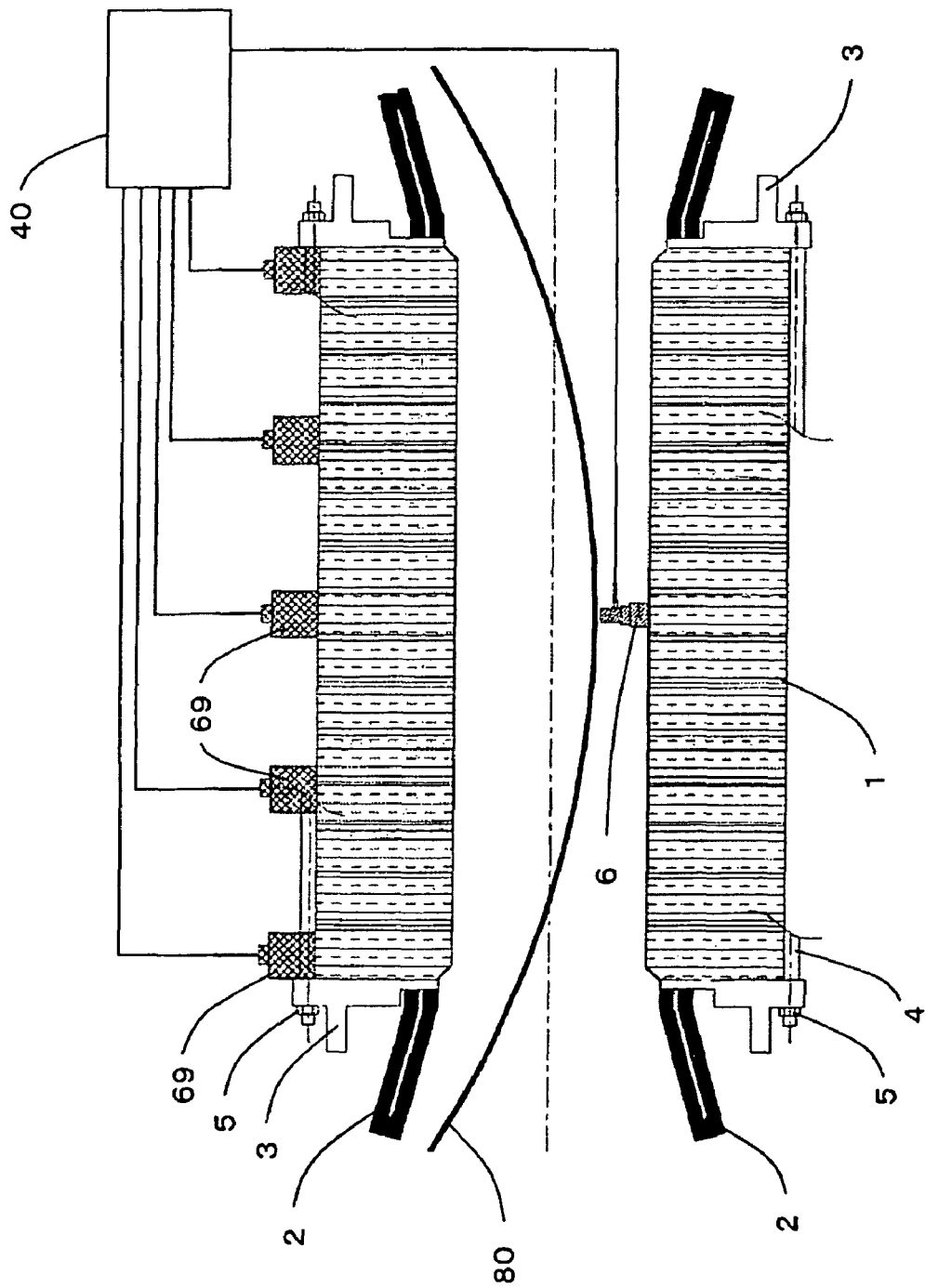
FIG. 19 is a longitudinal cross-sectional view schematically showing a fifth embodiment of a stator core of a rotary electrical machine and a stator core loosening diagnosis device.
Figure 20:
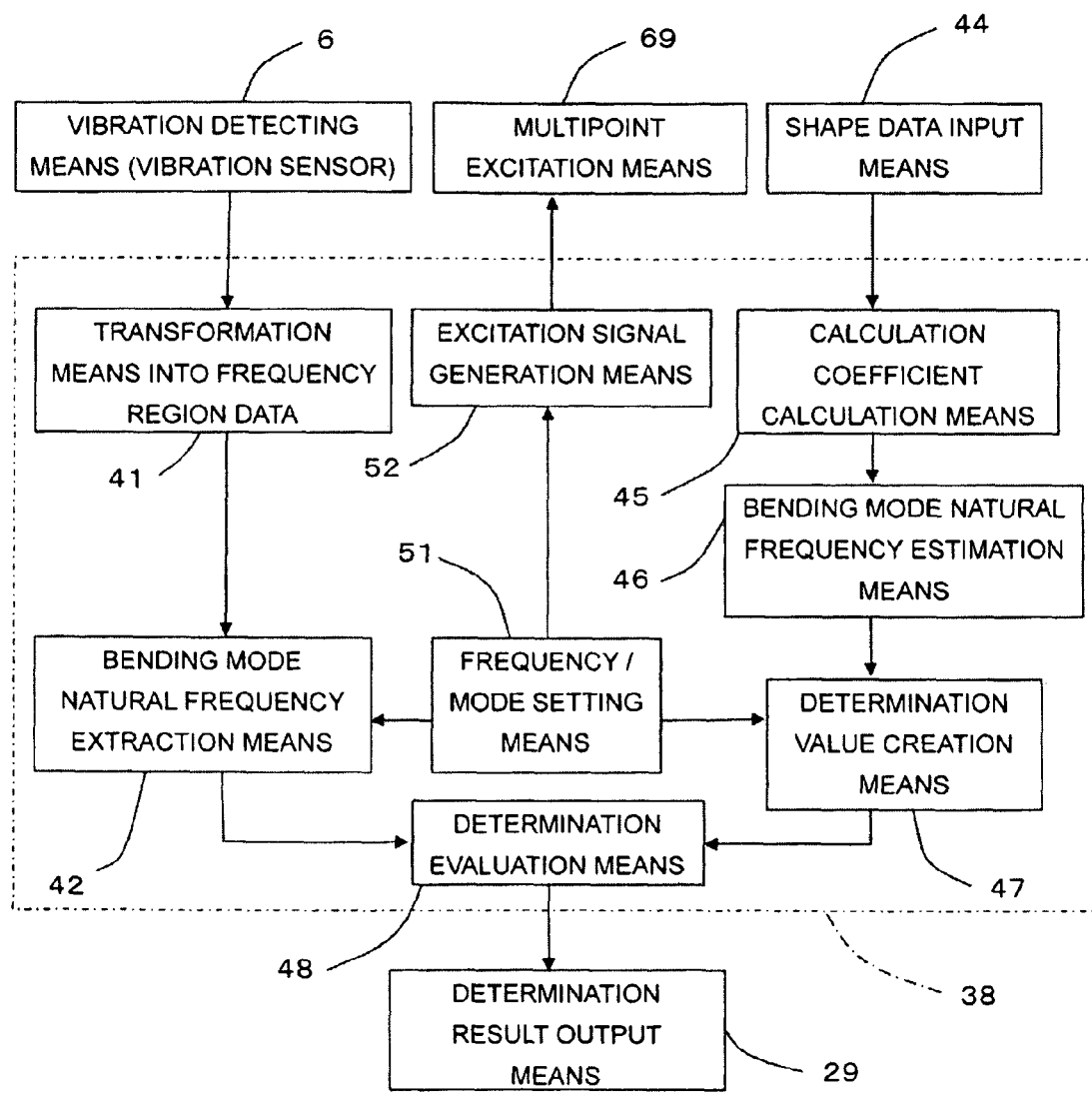
FIG. 20 is a block diagram showing a concrete example of a signal processing means shown in FIG. 19.

A fifth embodiment of the stator core loosening diagnosis device according to the present invention and rotary electrical machine incorporating the diagnosis device will be described below with reference to FIGS. 19 and 20. In FIGS. 19 and 20, the same reference numerals as those in the fourth embodiment denote the same or corresponding parts as those in the fourth embodiment, and the descriptions thereof will be omitted here. As in the fourth embodiment, the present embodiment focuses on the bending mode of the stator core.

In FIG. 19, multipoint excitation means 69 are each, e.g., an actuator such as an electromagnetic vibrator or a hydraulic vibrator. A given excitation force is obtained by inputting a signal to the actuator. A plurality of the multipoint excitation means 69 are rigidly fixed to the outer diameter surface of the stator core 1 and arranged in the axial direction thereof so as to vibrate the stator core 1 in the radial direction thereof. The multipoint excitation means 69 are vibrated by a single sine wave, a waveform obtained by superimposing a plurality of sine waves, a sine wave sweeping over a certain frequency range, a triangular wave, a rectangular wave, or a random wave. Further, in order to easily excite vibration in each vibration mode, a frequency/mode setting means 51 and a excitation signal generation means 52 bring the phases of the excitation forces of respective excitation means in-phase or out-of-phase with each other or adjust the amplitudes of the excitation forces.

As shown in FIG. 20, a signal processing means 40 of the present embodiment includes a frequency/mode setting means 51 and a excitation signal generation means 52 in addition to the components of the signal processing means 38 (FIG. 16) of the fourth embodiment.

In the present embodiment, the natural frequency in a required bending mode is sent from the frequency/mode setting means 51 not only to the excitation signal generation means 52 but also to the determination value creation means 47 and bending mode natural frequency extraction means 42. Thus, the generation of determination value and extraction of actual measurement natural frequency performed in each means are facilitated. A excitation signal generated by the excitation signal generation means 52 is sent to the multipoint excitation means 69. When vibration in a specified vibration mode is excited by the multipoint excitation means 69, the vibration sensor 6 detects the vibration of the stator core 1 in the excitation direction. In this case, the vibration mode in which vibration excited by the multipoint excitation means 69 is identified, so that it is not necessary to provide a plurality of vibration sensors 6 and it is sufficient to provide only one vibration sensor 6. The determination processing in the signal processing means 40 performed after the detection of the vibration sensor 6 is the same as that in the fourth embodiment except that the natural frequency extracted by the frequency/mode setting means 51 has already been determined.

In the stator core loosening diagnosis device of the rotary electrical machine according to the fifth invention having the above configuration, a plurality of multipoint excitation means 69 for vibrating the stator core 1 in the radial direction are arranged on the outer radial side of the stator core 1 in the axial direction thereof, and vibration is excited by a single wave, random wave, or sweeping wave with the phase and amplitude of the excitation signal of each multipoint excitation means 69 adjusted so as to excite vibration in the bending mode. Thus, vibration in a required bending mode is excited and thereby the stator core 1 correspondingly vibrates (e.g., in a U-like shape bending mode 80 shown in FIG. 19).

Therefore, the vibration signal detected by the vibration sensor 6 includes only a vibration signal of a required bending mode, making it easy for the bending mode natural frequency extraction means 42 to extract the natural frequency in the bending mode. This may eliminate the need to provide the bending mode natural frequency extraction means 42 in some cases. Further, it is possible to provide in a permanent manner the multipoint excitation means 69 and vibration sensor 6 inside the rotary electrical machine, so that the residual specific pressure of the stator core 1 can be monitored constantly or diagnosed periodically without a need of disassembling the rotary electrical machine.

Further, by vibrating the excitation means at the natural frequency in the previously calculated bending mode, a vibration signal of a required vibration mode can be detected and determined with high sensitivity. Furthermore, by exciting vibration using a random wave, or sweeping wave, the natural frequency in a target bending mode can be excited even if slightly deviated, enabling the vibration mode to be clearly grasped.

According to the present embodiment, the stator core 1 can be vibrated arbitrarily at the natural frequency in a specific vibration mode by a plurality of multipoint excitation means 69. This eliminates the need of arranging a plurality of vibration sensors 6 on the outer circumferential surface of the stator core 1 in the axial direction thereof, resulting in elimination of the need of determining the vibration mode from the signals from the vibration sensors 6 for extracting a specific vibration mode. In general, many databases are required to determine and extract a specific vibration mode from data obtained at limited measurement points. When the need of determining and extracting the vibration mode can be eliminated as in the case of the present embodiment, the configuration of the signal processing means can be simplified and measurement points can be reduced, resulting in a reduction of the time required for measurement and time required for determination.

Other Embodiments

The embodiments described above are merely given as examples, and it should be understood that the present invention is not limited thereto.

For example, by combining the loosening determination using the circular ring vibration mode described in the first to third embodiments and loosening determination using the bending mode described in the fourth and fifth embodiments, it is possible to perform more reliable loosening determination.

Further, acoustic or displacement sensor 11 in the third embodiment may be replaced by the vibration sensor 6 in the fourth or fifth embodiment.

What is claimed is:

1. A diagnosis device for diagnosing loosening of a stator core of a rotary electrical machine, the stator core being configured by laminating, in an axial direction, electromagnetic steel sheets on both or one of the surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis device comprising:
excitation means for vibrating the stator core in the radial direction thereof;
vibration detection means for detecting the vibration of the stator core in the radial direction;
means for frequency-analyzing an output signal of the vibration detection means that detects vibration generated in the stator core when the stator core is vibrated by the excitation means so as to extract a measurement natural vibration mode of the stator core in a circular ring natural vibration mode;
means for estimating a circular ring natural vibration mode of the stator core from shape data of the stator core; and
means for determining a clamping state of the stator core by comparing the measurement natural vibration mode and a determination criterion obtained based on the estimated natural vibration mode.

2. The stator core loosening diagnosis device according to claim 1, wherein:
the determination means calculates, as parameters, a natural frequency in the measurement natural vibration mode having a same mode shape with respect to a radial cross-section and having an axial direction in-phase mode and natural frequency in the measurement natural vibration mode having a same mode shape with respect to a radial cross-section and having an axial direction out-of-phase mode, natural frequency in an axial direction U-like shape vibration mode, S-like shape vibration mode, or W-like shape vibration mode, ratio between those natural frequencies, transfer function, or change in the natural frequency, and compares the calculated parameters and determination criteria indicated by relationships between parameters including natural frequency, ratio between those natural frequencies, transfer function, or change in the natural frequency, which are obtained from an estimated natural frequency in the same manner as the calculated parameters and stator core specific pressure so as to determine clamping state of the stator core.

3. The stator core loosening diagnosis device according to claim 1, wherein:
the determination means calculates a damping ratio from the measurement natural vibration mode and compares the calculated damping ratio and a determination criterion indicated by a relationship between a damping ratio previously estimated from shape data and stator core specific pressure so as to determine the clamping state of the stator core.

4. The stator core loosening diagnosis device according to claim 1, wherein:
the vibration detection means includes vibration sensors attached to axial direction both end portions of the stator core, and
the determination means calculates an amplitude ratio or transfer function in the measurement natural vibration mode and compares the calculated amplitude ratio or transfer function and a determination criterion indicated by a relationship between an amplitude ratio between axial direction both end vibrations or transfer function previously estimated from shape data and stator core specific pressure so as to determine the clamping state of the stator core.

5. The stator core loosening diagnosis device according to claim 1, wherein
the determination means combines a plurality of vibration parameters in the measurement natural vibration mode, including natural frequency, ratio between those natural frequencies, amplitude, damping ratio, ratio between axial direction both end amplitudes, or transfer function and compares the parameter combination and determination criterion so as to determine the clamping state of the stator core.

6. The stator core loosening diagnosis device according to claim 1, wherein:
the excitation means and vibration detection means are incorporated in the rotary electrical machine, and
the loosening state of the stator core can be monitored constantly or diagnosed periodically.

7. The stator core loosening diagnosis device according to claim 1, wherein the excitation means applies a vibration force to the stator core with a specified single frequency sine wave or a waveform obtained by superimposing a plurality of frequencies.

8. The stator core loosening diagnosis device according to claim 1, wherein the excitation means applies a vibration force to the stator core with a sine sweep waveform.

9. The stator core loosening diagnosis device according to claim 1, wherein the excitation means applies a vibration force to the stator core with a random waveform.

10. The stator core loosening diagnosis device according to claim 1, wherein the excitation means applies an impulse force to the stator core.

11. The stator core loosening diagnosis device according to claim 1, further comprising:
means for detecting the excitation force of the excitation means, and
the determination means calculates a natural frequency, amplitude, ratio between magnitude of damping ratio and excitation force, or transfer function, and compares them with a determination criterion indicated by a ratio between parameters and vibration force or relationship between the transfer function and stator core specific pressure so as to determine the clamping state of the stator core.

12. The stator core loosening diagnosis device according to claim 1, wherein the vibration detection means comprises a displacement sensor.

13. The stator core loosening diagnosis device according to claim 1, wherein the vibration detection means comprises an acoustic sensor.

14. A diagnosis device for diagnosing loosening of a stator core of a rotary electrical machine, the stator core being configured by laminating, in an axial direction, electromagnetic steel sheets on both or one of surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis device comprising:
   excitation means for vibrating the stator core in a lateral direction thereof;
   vibration detection means for detecting the vibration of the stator core in the excitation direction at a plurality of points arranged in axial direction of the stator core;
   means for frequency-analyzing an output signal of the vibration detection means that detects vibration generated in the stator core when the stator core is vibrated by the excitation means so as to extract a measurement natural frequency of the stator core in a bending mode;
   means for estimating a natural frequency of the stator core in the bending mode from shape data of the stator core;
   means for creating a determination value based on the estimated natural frequency; and
   determination means for determining the clamping state of the stator core by comparing the measurement natural frequency and determination value.

15. The stator core loosening diagnosis device according to claim 14, wherein the natural frequency in the bending mode based on which the clamping state of the stator core is determined is set to the natural frequency in one vibration mode which is selected from both-end free first-order mode, second-order mode, and third-order mode.

16. The stator core loosening diagnosis device according to claim 14, wherein the natural frequency in the bending mode based on which the clamping state of the stator core is determined is set to the natural frequencies in a plurality of vibration modes which are selected from both-end free first-order mode, second-order mode, and third-order mode.

17. The stator core loosening diagnosis device according to claim 14, wherein the means for estimating the estimated natural frequency of the stator core in the bending mode from shape data of the stator core regards the stator core as a both-end free beam and calculates the estimated natural frequency using a calculation formula for calculating the bending vibration of the beam.

18. The stator core loosening diagnosis device according to claim 17, wherein in the calculation formula for calculating the bending vibration of the beam, the stator core specific pressure is represented by changing a Young's modulus equivalent to the stator core specific pressure in the calculation formula for calculating the bending vibration of the beam.

19. The stator core loosening diagnosis device according to claim 17, wherein a shape correction coefficient previously created based on a ratio between outer and inner diameters of the stator core and a ratio between the outer or inner diameter of the stator core and axial direction length thereof is used to correct the calculation formula for calculating the bending vibration of the beam.

20. The stator core loosening diagnosis device according to claim 17, wherein in the calculation formula for calculating the bending vibration of the beam, a support condition correction coefficient previously created based on the support condition of the stator core is used to correct the calculation formula for calculating the bending vibration of the beam.

21. The stator core loosening diagnosis device according to claim 17, wherein:
   the excitation means vibrates the stator core at a plurality of points arranged in the axial direction of the stator core, and
   the vibration frequency, amplitude, and phase of the excitation force can be adjusted at respective excitation points.

22. A diagnosis method for diagnosing the loosening of a stator core of a rotary electrical machine, the stator core being configured by laminating, in axial direction, electromagnetic steel sheets on both or one of surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis method comprising:
   a excitation step of vibrating the stator core in the radial direction thereof;
   a vibration detection step of detecting the vibration of the stator core when the stator core is vibrated in the excitation step;
   a measurement natural vibration mode extraction step of frequency-analyzing an output signal of the vibration detection step so as to extract a measurement natural vibration mode of the stator core in a circular ring natural vibration mode;
   a natural vibration mode estimation step of estimating a circular ring natural vibration mode of the stator core from shape data of the stator core; and
   a determination step of determining a clamping state of the stator core by comparing the measurement natural vibration mode and a determination criterion obtained based on the estimated natural vibration mode.

23. A diagnosis method for diagnosing loosening of a stator core of a rotary electrical machine, the stator core being configured by laminating, in an axial direction, electromagnetic steel sheets on both or one of surfaces of which an insulation film is coated and which has, on its inner radial side, a space into which a coil is inserted, clamping the laminated electromagnetic steel sheets in the axial direction, inserting the coil into the coil insertion space formed on the inner radial side, and connecting the coil outside the stator core, the diagnosis method comprising:
   a excitation step of vibrating the stator core in a lateral direction thereof;
   a vibration detection step of detecting the vibration of the stator core at a plurality of points arranged in axial direction of the stator core when the stator core is vibrated in the excitation step;
   a measurement natural frequency extraction step of frequency-analyzing an output signal detected in the vibration detection step so as to extract a measurement natural vibration mode of the stator core in a bending mode;
   a natural frequency estimation step of estimating an estimated natural frequency of the stator core in the bending mode from shape data of the stator core; and
   a determination step of determining the clamping state of the stator core by comparing the measurement natural vibration mode and determination value obtained based on the estimated natural frequency.

* * * * *